United States Patent
Dykstra et al.

(10) Patent No.: US 6,956,013 B2
(45) Date of Patent: Oct. 18, 2005

(54) PHOTO-ACTIVATED PRO-FRAGRANCES

(75) Inventors: Robert Richard Dykstra, Cleves, OH (US); Gregory Scot Miracle, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 97 days.

(21) Appl. No.: 10/727,695

(22) Filed: Dec. 4, 2003

(65) Prior Publication Data

US 2004/0087454 A1 May 6, 2004

Related U.S. Application Data

(63) Continuation-in-part of application No. 10/106,707, filed on Mar. 26, 2002, now abandoned.
(60) Provisional application No. 60/282,789, filed on Apr. 10, 2001.

(51) Int. Cl.⁷ .............................. C11D 3/50; A61K 7/46; C07C 69/78
(52) U.S. Cl. .............................. 510/107; 512/20; 560/55
(58) Field of Search .................... 510/107; 512/20; 560/55

(56) References Cited

U.S. PATENT DOCUMENTS

| | | | |
|---|---|---|---|
| 3,234,258 A | 2/1966 | Morris | |
| 3,547,903 A | * 12/1970 | Hooper et al. | ............. 536/17.4 |
| 3,929,678 A | 12/1975 | Laughlin et al. | |
| RE29,814 E | 10/1978 | Snyder | |
| 4,565,647 A | 1/1986 | Llenado | |
| 4,597,898 A | 7/1986 | Vander Meer | |
| 5,075,041 A | 12/1991 | Lutz | |
| 5,339,769 A | 8/1994 | Toth et al. | |
| 5,349,101 A | 9/1994 | Lutz et al. | |
| 5,389,277 A | 2/1995 | Prieto | |
| 5,454,982 A | 10/1995 | Murch et al. | |
| 5,486,303 A | 1/1996 | Capeci et al. | |
| 5,489,392 A | 2/1996 | Capeci et al. | |
| 5,489,393 A | 2/1996 | Connor et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,691,297 A | 11/1997 | Nassano et al. | |
| 6,156,710 A | 12/2000 | Sivik et al. | |

FOREIGN PATENT DOCUMENTS

| | | | |
|---|---|---|---|
| DE | 1058067 | * | 5/1959 |
| EP | 0 905 115 A1 | | 3/1999 |
| EP | 936 211 A2 | | 8/1999 |
| EP | 983990 | * | 3/2000 |
| GB | 2 352 179 A | | 1/2001 |
| WO | WO 95/10603 | | 4/1995 |
| WO | WO 97/34986 A | | 9/1997 |
| WO | WO 02/38120 A1 | | 5/2002 |

OTHER PUBLICATIONS

B.F. Bonini et al., *Chemistry of silyl thioketones. Part 10. Synthesis and reactivity of α–silyl vinyl sulfides*, J. Chem. Soc., Perkin Trans. 1, 1996, pp. 2803–2809.
G. Bellucci et al., *Crown Ether Catalyzed Stereoselective Synthesis of Vinyl Ethers in a Solid Liquid Two–Phase System*, Synlett, Sep. 1996, pp. 880–882.
Arctander S. "Perfume and Flavor Chemicals, Passage" 1969, Perfume and Flavor Chemicals Aroma S. Artctander, US. vol. vol. 2, XP–002062565.
Beller, Matthias et al. "Oxidative Anti–Markovnikov–amination of aromatic Olefins", Chemical Industries (Dekker), 1998, 75, (Catalysis of Organic Reactions), 319–332.

* cited by examiner

*Primary Examiner*—John R. Hardee
(74) *Attorney, Agent, or Firm*—James F. McBride; Kim W. Zerby; Steve W. Miller

(57) ABSTRACT

The first aspect of the present invention relates to a photo-activated pro-accord conjugate having the formula:

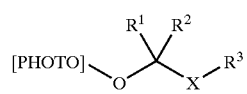

wherein [PHOTO] is a photo-labile unit which upon exposure to electromagnetic radiation is capable of releasing a pro-accord unit; X is selected from oxygen, nitrogen, sulfur; $R^1$ and $R^2$ are moieties when taken together comprise an aldehyde or a ketone fragrance raw material, and $R^3$ comprises hydrogen, a fragrance raw material alcohol, an amine, or a thio compound.

16 Claims, No Drawings

PHOTO-ACTIVATED PRO-FRAGRANCES

CROSS REFERENCE TO RELATED APPLICATIONS

This application is a continuation-in-part of U.S. application Ser. No. 10/106,707, filed Mar. 26, 2002 now abandoned, which in turn claims priority under 35 U.S.C. § 119(e) to U.S. Provisional Application Ser. No. 60/282,789 filed Apr. 10, 2001.

FIELD OF THE INVENTION

The present invention relates to photo-labile pro-accord conjugates, which are capable of releasing a fragrance raw material accord in a sequence of chemical reaction steps beginning with a photo-activated release of an oxygen-containing pro-fragrance compound. The conjugates are useful in formulating fragrance delivery systems. The conjugates of the present invention are capable of delivering fragrance raw materials.

BACKGROUND OF THE INVENTION

Pro-fragrances and pro-accords have been used to enhance the delivery of fragrance raw materials and to sustain their duration. Typically pro-fragrances and pro-accords deliver alcohol, ketone, aldehyde, and ester fragrance raw materials via substrates which are hydrolyzed by one or more mechanisms, inter alia, the acidic pH of skin, nascent moisture.

Fragrances or odors not only provide a pleasant aesthetic benefit, but also serve as a signal. Therefore, the delivery of an aroma sensory signal is also a benefit, which a pro-fragrance can provide.

Pro-fragrances and pro-accords typically rely on the break down of a chemical species not based on accidental circumstance but on deliberate execution. The present invention provides a means for delivering a fragrance or an accord wherein the delivery of said fragrance or said accord may be instigated by exposure to a trigger such as light.

SUMMARY OF THE INVENTION

It has been surprisingly discovered that a fragrance accord can be delivered by photo-activated pro-accord conjugates. The photo-labile conjugates of the present invention are activated by the exposure of the conjugates to electromagnetic radiation, which is the first step in a chemical cascade resulting in the ultimate release of a fragrance raw material. The first step in the cascade involves photochemical induced fragmentation of a chemical bond between (a) an oxygen atom contained within a fragrance precursor portion and (b) a photochemically activated triggering unit.

The conjugates of the present invention can be deposited onto surfaces such as hair, skin and fabric. For example, a treated fabric may be stored, inter alia, kept in a drawer, closet, and when worn or used at a later time, is exposed to electromagnetic radiation which begins the cascade releasing the pro-accord.

The first aspect of the present invention relates to a photo-activated pro-accord conjugate having the formula:

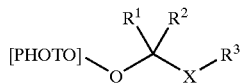

wherein [PHOTO] is a photo-labile unit which upon exposure to electromagnetic radiation is capable of releasing a pro-accord unit;

X is:
a.) —O—;
b.) —NH—;
c.) —S—;
d.) —NR$^7$—;
e.) —N(R$^8$)$_2$—
f.) or mixtures thereof;
wherein R$^7$, and each R$^8$ is independently selected from
  i) $C_1$–$C_{20}$ substituted or unsubstituted, linear or branched, cyclic or acyclic hydrocarbyl;
  ii) $C_3$–$C_{20}$ substituted or unsubstituted, cyclic or acyclic heterocarbyl;
  iii) $C_6$–$C_{20}$ substituted or unsubstituted alkaryl, aryl or aralkyl;
  iv) or mixtures thereof;

R$^1$ is selected from:
a.) $C_1$–$C_{20}$ substituted or unsubstituted, linear or branched, cyclic or acyclic hydrocarbyl;
b.) $C_3$–$C_{20}$ substituted or unsubstituted, cyclic or acyclic heterocarbyl;
c.) or mixtures thereof;

R$^2$ is selected from:
a.) hydrogen;
b.) R$^1$;
wherein R$^1$ and R$^2$ are moieties when taken together with a carbonyl moiety comprise an aldehyde or a ketone having the formula:

which is capable of being released by said photo labile compound; and

R$^3$ is selected from:
a.) $C_1$–$C_{20}$ substituted or unsubstituted, linear or branched, cyclic or acyclic hydrocarbyl;
b.) $C_3$–$C_{20}$ substituted or unsubstituted, cyclic or acyclic heterocarbyl;
c.) hydrogen;
d.) or mixtures thereof;
wherein when any 2 or more moieties selected from any non-hydrogen R$^3$, R$^7$ or R$^8$, combine, said moieties form a common ring.

Additional aspects of the present invention relate to a system for delivering a fragrance accord and a method for delivering an accord to a situs.

These and other objects, features, and advantages will become apparent to those of ordinary skill in the art from a reading of the following detailed description and the appended claims.

DETAILED DESCRIPTION OF THE INVENTION

The present invention relates to the surprising discovery that a perfume raw material accord can be delivered by a photo-activated pro-accord conjugate. The compounds of the present invention are more stable than the corresponding pro-fragrance compound. Previous pro-accords were compounds, which were capable of delivering fragrance raw material accords via a one step break down of a pro-accord molecule. Said molecules were susceptible to pre-mature breakdown if the release was kinetically rapid, or thermodynamically favored in the presence of nascent moisture. The compounds of the present invention are conjugates, which comprise an aldehyde or ketone in a releasable form such as a hemiacetal, a hemiaminal, or a hemithioacetal. In one embodiment, the hemiacetal formed is capable of releasing a fragrance raw material alcohol. In addition, the photo-labile moiety, which initiates breakdown of the conjugate may also take the final form of a fragrance raw material or a component that has desirable aesthetic properties, such as coumarin which is widely used in perfumes. One aspect of the present invention, which leads to many embodiments, relates to the admixing of photo-activated pro-accord conjugates that are comprised of aesthetically related fragrance raw materials.

Conjugates may be directly or indirectly applied. Examples of products wherein said conjugates are typically directly applied via contacting a situs with a finished product comprising one or more conjugates include, but are not limited to, fine fragrance perfume applications or beauty care products, such as creams, lotions, deodorants, antiperspirants, nail polish and other topical compositions; hair care products, such as hair spray, hair gels, and leave-in conditioners, fabric static control sheets, fabric and carpet refresher sprays, air fresheners; paper products such as diapers, toilet paper, and cleaning wipes; and food and related products such as coffee and pet food. Examples of products comprising one or more conjugates wherein said conjugates are typically indirectly applied include, but are not limited to, body wash, bar soaps, hair and/or body shampoos, hair and/or body conditioners, pet shampoos and/or conditioners, hair colorants, laundry or cleaning product such as detergents, fabric softeners, hard surface cleaners, carpet cleaners—such products are typically diluted with a diluent before or during use.

Definitions

For purposes of the present invention the term "situs" includes hair, skin, nails, fabric, paper products, nonwovens, pet litter, foods, beverages and hard surfaces.

For the purposes of the present invention the terms "photo-labile" and "photo-activated" are synonymous.

For the purposes of the present invention the term "photo-labile unit" and "photo-labile moiety" are synonymous.

For the purposes of the present invention the term "photo-labile unit" is defined herein as "a unit, which upon exposure to electromagnetic radiation acts to begin the cascade of chemical transformations which ultimately release the fragrance raw material or fragrance accord." In some embodiments of the present invention, for example, a hemiaminal form of the conjugate wherein an amine is released, it may be advantageous that the released amine compound does not interfere with the aesthetic quality or character of the released fragrance raw material or accord. In the presence of light, the photo-labile unit serves to trigger the chemical reaction or reaction cascade that ends with the ultimate release of one or more fragrance raw materials.

For the purposes of the present invention the term "Pro-fragrance unit" is defined herein as "that portion of the photo-labile pro-fragrance conjugate, which gives rise to the fragrance compound or pro-fragrance compound as a result of exposure of the photo-labile pro-fragrance conjugate to electromagnetic radiation."

For the purpose of the present invention the term "pro-accord conjugate" is defined herein as "a chemical species, which by undergoing one or more chemical transformations results in the release of one or more fragrance compounds." Fragrance compounds and fragrance raw materials are terms, which refer to the final "perfume" ingredients, which are delivered and are used interchangeably herein. The term "chemical transformation" includes conversion to a species of different molecular formula by any means, inter alia, hydrolysis, photolysis, thermolysis, autoxidation, addition, elimination and substitution reactions, as well as conversion to a species with the same molecular formula, but having an altered chemical orientation, i.e., isomerized.

The chemical cascade, which begins the release of a fragrance raw material, may be controlled by requiring a certain wavelength of electromagnetic radiation to be present to initiate the release sequence. For example, "outside light", which typically comprises the full range of UV light, may be required to initiate the release of the fragrance precursor.

Mixtures of fragrance materials are known by those skilled in the art of fragrances and perfumes as "accords". The term "accord" as used herein is defined as "a mixture of two or more 'fragrance raw materials', which are artfully combined to impart a pleasurable scent, odor, essence, or fragrance characteristic". For the purposes of the present invention, some conjugates which comprise one or more embodiments of the present invention may release only one fragrance raw material, however, these materials are also referred to as photo-activated pro-accord conjugates. For the purposes of the present invention "fragrance raw materials" are herein defined as compounds having a molecular weight of at least 100 g/mol and which are useful in imparting an odor, fragrance, essence, or scent either alone or in combination with other "fragrance raw materials".

The term "hydrocarbyl" relates to any hydrocarbon chain having from 1 to 20 carbon atoms. The chains may be linear, inter alia, octyl, and decyl; or branched, inter alia, 6-methyl octyl. The chains may be acyclic; alkyl, alkenyl, alkynyl, and the like, or cyclic, for example, cyclohexyl, or bicyclo [2.2.1]heptanyl. The term hydrocarbyl also encompasses any type of chain branching of the units such that the total number of carbon atoms in said chain is from 1 to 20. Hydrocarbyl units may be aromatic or non-aromatic.

The term "heterocarbyl" is used herein throughout the specification to mean a unit comprising from 3 to 20 carbon atoms wherein at least one atom in the main chain, or ring is a heteroatom. Several embodiments of the present invention comprise one or more heteroatoms selected from the group consisting of oxygen, nitrogen, sulfur, and mixtures thereof. Heterocarbyl units may be aromatic or non-aromatic. Non-limiting examples of heterocarbyl units include piperidine, ketopiperazine, ketodiazepine, proline, piperazine, pyrroline, and pyrrolidone.

The term "substituted" is defined as "replacement of a hydrogen atom, two hydrogen atoms, or three hydrogen atoms from a carbon atom to form a moiety, or the replacement of hydrogen atoms from adjacent carbon atoms to form a moiety." For example, a substituted unit that requires a single hydrogen atom replacement includes halogen, hydroxyl, and the like. A two-hydrogen atom replacement includes carbonyl, oximino, and the like. Three hydrogen replacements includes cyano, and the like. The term substituted is used to indicate that a moiety, inter alia, aromatic ring, alkyl chain, can have one or more of the hydrogen atoms replaced by a substituent. For example, 4-hydroxyphenyl is a "substituted aromatic carbocyclic ring", and 3-guanidinopropyl is a "substituted $C_3$ alkyl unit."

The following are non-limiting examples of moieties, which can replace hydrogen atoms on carbon to form substituted units:

i) —NHCOR$^5$;
ii) —COR$^5$;
iii) —COOR$^5$;
iv) —COCH=CH$_2$;

v) —C(=NH)NH$_2$;
vi) —N(R$^5$)$_2$;
vii) —NHC$_6$H$_5$;
viii) =CHC$_6$H$_5$;
ix) —CON(R$^5$)$_2$;
x) —CONHNH$_2$;
xi) —NHCN;
xii) —OCN;
xiii) —CN;
xiv) —F, —Cl, —Br, —I, and mixtures thereof;
xv) =O;
xvi) —OR$^5$;
xvii) —NHCHO;
xviii) —OH;
xix) —NHN(R$^5$)$_2$;
xx) =NR$^5$;
xxi) =NOR$^5$;
xxii) —NHOR$^5$;
xxiii) —CNO;
xxiv) —NCS;
xxv) =C(R$^5$)$_2$;
xxvi) —SO$_3$M;
xxvii) —OSO$_3$M;
xxviii) —SCN;
xxix) —P(O)H$_2$;
xxx) —PO$_2$;
xxxi) —P(O)(OH)$_2$;
xxxii) —SO$_2$NH$_2$;
xxxiii) —SO$_2$R$^5$;
xxxiv) —NO$_2$;
xxxv) —CF$_3$, —CCl$_3$, —CBr$_3$;
xxxvi) and mixtures thereof;
wherein R$^5$ is hydrogen, C$_1$–C$_{20}$ linear or branched alkyl, C$_6$–C$_{20}$ aryl, C$_7$–C$_{20}$ alkylenearyl, and mixtures thereof; M is hydrogen, or a salt forming cation. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

All percentages, ratios and proportions herein are by weight, unless otherwise specified. All temperatures are in degrees Celsius (° C.) unless otherwise specified. All documents cited are in relevant part, incorporated herein by reference.

Photo-activated Pro-accords

The photo-activated pro-accord conjugates of the present invention are capable of releasing an aldehyde having the formula R$^1$CHO or a ketone having the formula R$^1$R$^2$CO, together with a molecule having the formula R$^3$XH, inter alia, alcohols, which are the constituents of a fragrance raw material comprising accord. The conjugates have the formula:

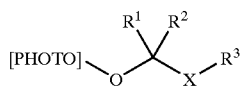

wherein [PHOTO] is a photo-labile unit which upon exposure to electromagnetic radiation is capable of releasing a pro-accord unit. The [PHOTO] unit itself may also take the final form of a fragrance raw material or a component that has desirable aesthetic properties or enhances formulation of the conjugate.

In said formula, X is a moiety selected from:
a.) —O—;
b.) —NH—;
c.) —S—;
d.) —NR$^7$—
e.) —N(R$^8$)$_2$—
f.) or mixtures thereof;
wherein R$^7$, and each R$^8$ is independently selected from
i) C$_1$–C$_{20}$ substituted or unsubstituted, linear or branched, cyclic or acyclic hydrocarbyl;
ii) C$_3$–C$_{20}$ substituted or unsubstituted, cyclic or acyclic heterocarbyl;
iii) C$_6$–C$_{20}$ substituted or unsubstituted alkaryl, aryl or aralkyl;
iv) or mixtures thereof;

R$^1$ units are selected from the group consisting of:
a.) C$_1$–C$_{20}$ substituted or unsubstituted, linear or branched, cyclic or acyclic hydrocarbyl;
b.) C$_3$–C$_{20}$ substituted or unsubstituted, cyclic or acyclic heterocarbyl;
c.) or mixtures thereof R$^2$ is selected from:
a.) hydrogen;
b.) R$^1$;
wherein R$^1$ and R$^2$ are moieties when taken together with a carbonyl moiety comprise an aldehyde or a ketone having the formula:

R$^1$R$^2$C=O which is capable of being released by said photo labile compound.

In the pro-accord, the carbonyl unit is in the form of an hemiacetal, hemiaminal, hemithioacetal and the like, depending upon whether X is oxygen, nitrogen, or sulfur. For the purposes of the present invention, solely as a matter of convention, when a ketone fragrance raw material is released by the conjugate, R$^1$ will represent the larger unit comprising said ketone. For, example, if the ketone released is β-ionone, the R$^1$ unit will represent the cyclic hydrocarbyl (cyclohexenyl)ethylene unit having the formula:

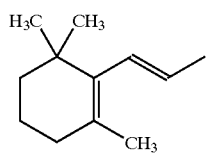

As indicated herein above, R$^1$ and R$^2$ are moieties which when taken together with the carbonyl carbon comprise an aldehyde or a ketone which is capable of being released by said photo-labile compound. For the purposes of the present invention, solely as a matter of convention, when a ketone fragrance raw material is released by the conjugate, R$^2$ will represent the smaller unit comprising said ketone. For example, for the various ionones, R$^2$ is methyl.

R$^3$ units are derived from units having the formula R$^3$OH, R$^3$NH$_2$, R$^3$NR$^7$, R$^3$N(R$^8$)$_2$ and R$^3$SH. For one embodiment of the present invention, wherein the conjugate releases fragrance raw material alcohols, R$^3$ units comprise alcohols having the formula R$^3$OH, wherein said alcohol has a molecular weight of at least 100 g/mol as defined herein above. Wherein when any moieties selected from any non-hydrogen $R^3$, $R^7$ or $R^8$ combine, said moieties form a common ring.

In one aspect of the conjugates of the present invention, the [PHOTO] unit is a (2-hydroxyphenyl) acrylic acid derivative having the formula:

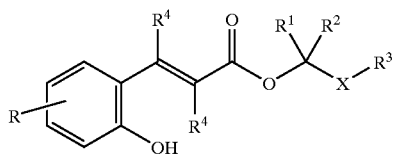

which is capable of releasing a coumarin derivative as the by-product of the photo initiation step.

In one embodiment of this aspect of the present invention, wherein an accord comprising a fragrance raw material alcohol, as well as a ketone or aldehyde is released, the X is an oxygen thereby forming a conjugate having the formula:

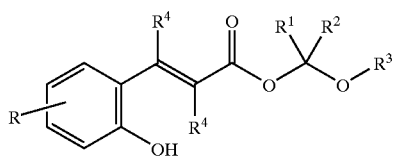

wherein said conjugate has the capacity of releasing the following compounds after a reaction cascade initiated by photo-cleavage of the photo-labile moiety:

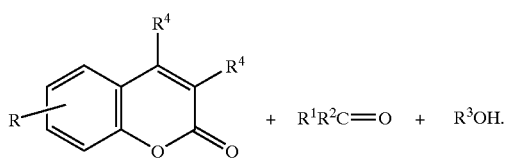

In another embodiment of this aspect of present invention, wherein a ketone or aldehyde is released, the moiety X is —N(H)—, $R^3$ and $R^4$ is hydrogen, and R is —OH, thereby forming a conjugate having the formula:

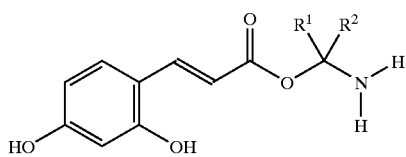

wherein said conjugate has the capacity of releasing the following compounds after a reaction cascade initiated by photo-cleavage of the photo-labile moiety:

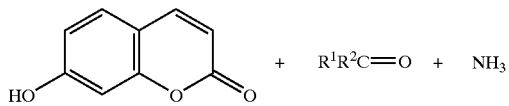

In another aspect of present invention, wherein a ketone or aldehyde is released, the moiety X is —N($R^7$)—, and $R^3$ is —CH$_2$CH$_2$OCH$_2$CH$_2$OCH$_3$, thereby forming a conjugate having the formula:

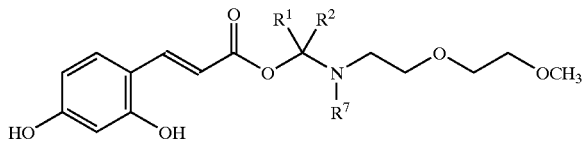

wherein said conjugate has the capacity of releasing the following compounds after a reaction cascade initiated by photo-cleavage of the photo-labile moiety:

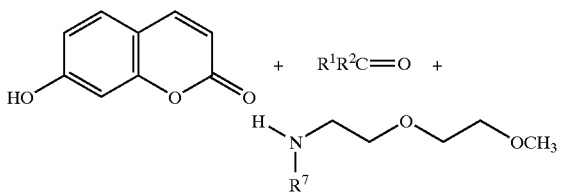

In another aspect of present invention, wherein a ketone or aldehyde is released, the moiety X is —N($R^8$)$_2$—, wherein the $R^8$ moieties combine to form a common ring, $R^3$ is —CH$_3$, R is —NH$_2$, and Y$^-$ is an anionic counter ion, thereby forming a conjugate having the formula:

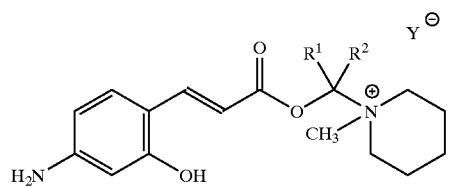

wherein said conjugate has the capacity of releasing the following compounds after a reaction cascade initiated by photo-cleavage of the photo-labile moiety:

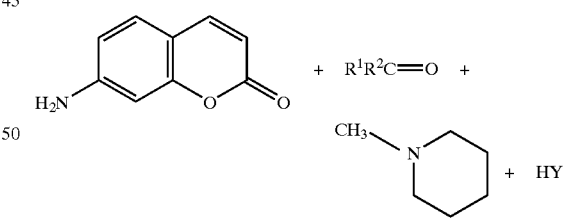

In another aspect of present invention, wherein a ketone or aldehyde is released, the moiety X is —N(H)—, and $R^3$ is —(CH$_2$)$_9$CH$_3$, thereby forming a conjugate having the formula:

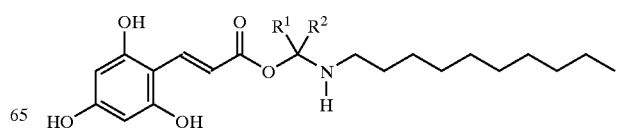

wherein said conjugate has the capacity of releasing the following compounds after a reaction cascade initiated by photo-cleavage of the photo-labile moiety:

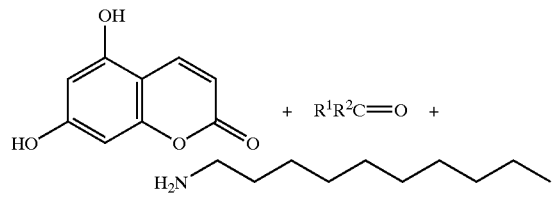

In the aforementioned embodiments, each R is hydrogen or a photo-labile unit modulating group that, without being bound by theory, is believed to alter the degree of electronic donation or withdrawal from the photo-labile unit, or modify the conjugate's degree of hydrophobicity.

R may be independently selected from the group consisting of:
 i) hydrogen;
 ii) halogen;
 iii) —OR';
 iv) —N(R')$_2$;
 v) —SR';
 vi) nitrilo;
 vii) $C_1$–$C_{20}$ substituted or unsubstituted, linear or branched, cyclic or acyclic hydrocarbyl;
 viii) and mixtures thereof;
wherein each R' unit is independently selected from the group consisting of hydrogen, $C_1$–$C_{20}$ hydrocarbyl, —OH, and mixtures thereof.

$R^4$ may be independently selected from the group consisting of:
 i) hydrogen;
 ii) halogen;
 iii) —OR';
 iv) —N(R')$_2$;
 v) —SR';
 vi) nitrilo;
 vii) a carbonyl comprising unit having the formula:

wherein $R^6$ is hydrogen, —OR', —N(R')$_2$, $C_1$–$C_{20}$ substituted or unsubstituted, linear or branched, cyclic or acyclic hydrocarbyl, $C_3$–$C_{20}$ substituted or unsubstituted, cyclic or acyclic heterocarbyl, or mixtures thereof;
 viii) $C_1$–$C_{20}$ substituted or unsubstituted, linear or branched, cyclic or acyclic hydrocarbyl;
 ix) or mixtures thereof.

In one embodiment of this aspect of the present invention, the released coumarin compound is a derivative that is odorless or that has a high odor detection threshold (ODT). In this embodiment R is —OH, such as when the photo-labile unit derived from 2,4-dihydroxycinnamoyl is finally release as the essentially odorless 7-hydroxycoumarin.

In another embodiment, the released coumarin compound has a low ODT. In this embodiment R is —H, such as when the photo-labile unit derived from 2-hydroxycinnamoyl is finally released as the low ODT coumarin.

Fragrance Accord Delivery Systems

One aspect of the present invention relates to systems for delivering fragrance accords to a situs. The systems of the present invention comprise:
 a) from about 0.0001% (1 ppm) by weight, of a photo-activated pro-accord conjugate according to the present invention; and
 b) the balance carriers and other adjunct ingredients.

In one embodiment of the present invention, the systems comprise from about 0.001% (10 ppm) to about 1% (10,000 ppm), or even to about 5% (50,000 ppm) by weight of conjugate. Still further embodiments of the present invention relate to systems comprising from about 0.05% (500 ppm) to about 0.5% (5000 ppm) by weight, of conjugate.

Said system may comprise a sufficient amount of carriers and other adjunct ingredients such that said system comprises a product selected from the group consisting of a hair care product, beauty care product, a laundry or cleaning product, a food or beverage product, a paper product, a pet care product or mixtures thereof. Examples of such products include, but are not limited to, a product selected from the group consisting of a cream, a lotion, a deodorant, an antiperspirant, a nail polish, a hair spray, a hair gel, a leave-in conditioner, a fabric static control sheet, a fabric refresher spray, a carpet refresher spray, an air freshener, a diaper, a toilet paper, a cleaning wipe; a food, a coffee, a pet food, a body wash, a bar soap, a hair shampoo, a body shampoo, a hair conditioner, a body conditioner, a pet shampoo, a pet conditioner, a hair colorant, a laundry detergent, a fabric softener, a hard surface cleaner, and a carpet cleaner. The aforementioned products may be combined to provide, for example, a shampoo and conditioning benefit or a detergent and fabric softening benefit.

In another aspect of the present invention, a mixture of two or more photo-activated pro-accord conjugates are admixed together. In another embodiment, complimentary fragrance raw materials can be released by the photo-activated pro-accord conjugates. For example, the pro-accord comprising geraniol and citronellal, can be delivered from a photo-activated pro-accord having the formula:

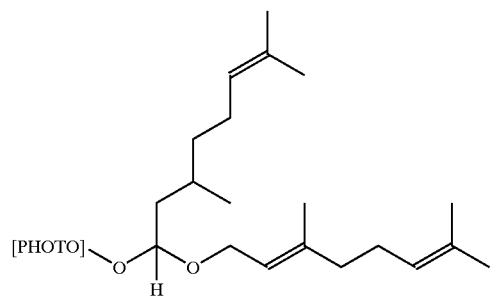

wherein [PHOTO] represents a photo-labile unit which initiates the fragrance raw material release cascade.

Another example, is the photo-activated pro-accord having the formula:

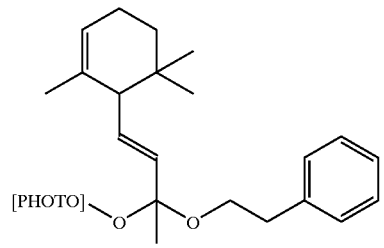

which is capable of releasing alpha-ionone and 2-phenylethanol.

EXAMPLE 1

Preparation of (E)-3-[2-hydroxyphenyl]-acrylic acid 1-heptyloxy-2-phenylethyl ester

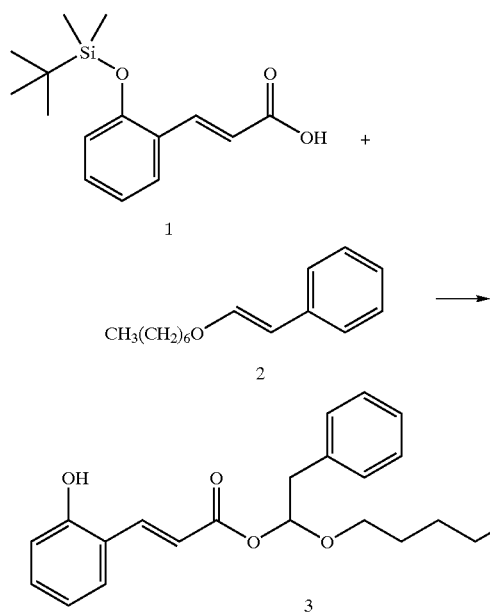

A solution of 6.5 g of (E)-3-[2-(tert-Butyl-dimethyl-silanoxy)-phenyl]-acrylic acid (1; prepared according to EP 0 936 211 A2) and 5.4 g of (E)-2-(heptyloxy)ethenyl benzene (2; prepared according to Bellucini, et al. *Synlett* 1996, 9, 880–882) in 25 mL of toluene is heated to reflux and stirred for 16 h. After cooling to room temperature and concentrating, the reaction mixture is purified by flash column chromatography to yield 7.2 g of the intermediate (E)-3-[2-(tert-Butyl-dimethyl-silanoxy)-phenyl]-acrylic acid 1-heptyloxy-2-phenylethyl ester. The intermediate is dissolved in 50 mL THF, cooled with an ice-water bath and treated for 30 min with 4.7 g of tetrabutylammonium fluoride. The mixture is thereafter concentrated and purified by flash chromatography to yield the title compound 3.

EXAMPLE 2

Preparation of (E)-3-[2-hydroxyphenyl]-acrylic acid 1-(2-propenylthio)-2-phenylethyl ester

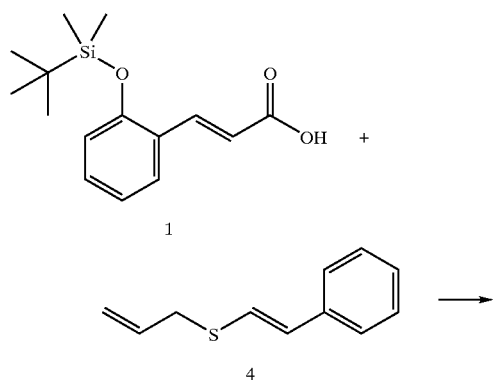

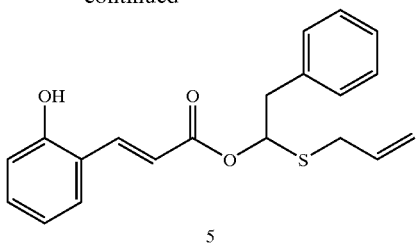

The title compound 5 is prepared according to the procedure of Example 1, substituting an equimolar amount of 2-(2-propenylthio)ethenyl benzene (4; prepared according to Bonini, et al. *J. Chem. Soc., Perkin Trans.* 1 1996, 23, 2803–2809) for 2.

EXAMPLE 3

Preparation of (E)-3-[2,4-dihydroxyphenyl]-acrylic acid 1-(2-methoxyethylamino)-2-phenylethyl ester

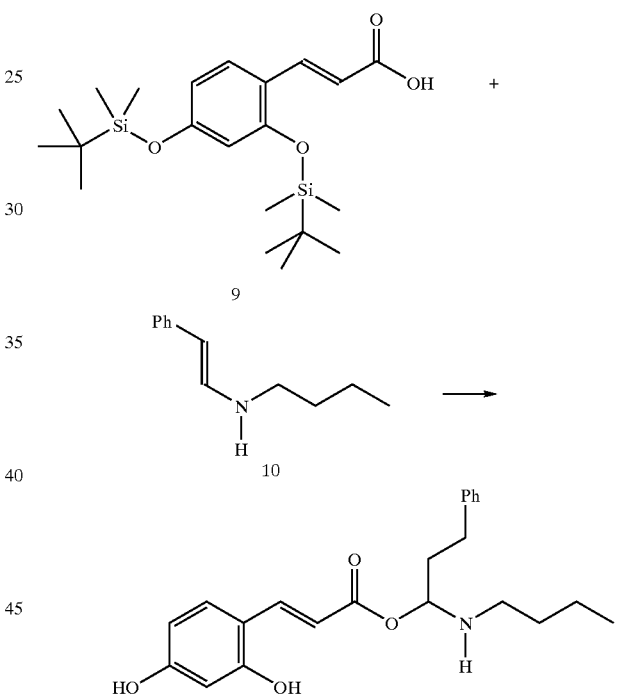

The title compound 11 is prepared according to the procedure of Example 1, substituting an equimolar amount of molecule 9 (prepared according to WO 02/038120) for molecule 1 and an equimolar amount of molecule 10 for molecule 2. Molecule 10 is prepared according to the procedure described in Beller, Matthias et al. Oxidative anti-Markovnikov-amination of aromatic olefins; Chemical Industries (Dekker) (1998), 75, (Catalysis of Organic Reactions), 319–332.

Method of Use

Another aspect of the present invention relates to a method of delivering a photo-activated pro-accord conjugate to a situs, said method comprising the step of contacting a situs with the photo-activated pro-accord conjugate of the present invention.

Another aspect on the present invention relates to a method for delivering an accord to a situs, said method comprising the steps of:
A) delivering to a situs a photo-activated pro-accord conjugate according to the present invention; said pro-accord capable of releasing one or more fragrance raw materials; and
B) exposing said pro-accord to electromagnetic radiation capable of initiating release of said fragrance raw materials.

Embodiments

The following are additional non-limiting embodiments of the present invention.

Skin Conditioning Lotions

An example of a skin care composition of the present invention comprises an ester having a total number of carbon atoms in excess of about 28, for example lauryl laurate, lauryl myristate, myristyl myristate, behenyl caprate, cetearyl palmitate, behenyl stearate, more preferably cetearyl palmitate and cetyl stearate.

The present compositions in addition to the esters described herein above, contain an emollient material in an amount such that the amount of ester plus emollient is from about 0.2%, preferably from about 4% to about 25%, preferably to about 18% of the total composition. One function of the emollient is to ensure that the ester is plasticized sufficiently to allow it to be in a film-like state on the skin. The emollient in the present compositions is selected from the group consisting of fatty alcohols, esters having fewer than about 24 total carbon atoms (e.g. isopropyl palmitate), branched chain esters having greater than about 24 total carbon atoms (e.g. cetearyl octonate), squalane, liquid or solid paraffins, mixtures of fatty acids and squalane, mixtures of fatty acids and liquid or solid paraffins and mixtures thereof. The aforementioned esters, those having fewer than 24 carbon atoms or branched and having more than 24 carbon atoms, if used as an emollient should preferably be used in an mount equal to about a third of the long chain ester. The particular emollient selected depends in part on the particular ester selected since proper plasticization, as indicated above, is desired. The emollient for the esters having more than 28 carbon atoms is preferably selected from the group consisting of squalane, liquid or solid paraffins and mixtures of fatty alcohols with squalane or paraffins. Typical fatty alcohols and fatty acids useful in the present compositions include those having from 12–22 carbon atoms such as cetyl alcohol, myristyl alcohol, stearyl alcohol, stearic acid and palmitic acid. Paraffins include, for example, mineral oil, petrolatum and paraffin wax. It is preferred that distilled water be used in the present compositions.

Optional Components

Oil Phase Components

In addition to the long chain esters, emollients and emulsifiers described previously, the oil phase of the present compositions may contain a variety of materials including:
(a) Esters not meeting the requirements for the long chain ester and not present as an emollient, supra, such as oleyl oleate, isostearyl isostearate, isopropyl lanolate, isopropyl myristate, butyl stearate, myristyl lactate and 2-ethyl hexyl palmitate;
(b) Oils such as castor oil, jojoba oil, cottonseed oil, peanut oil and sesame oil;
(c) Waxes such as ceresin wax, carnuba wax, beeswax and castor wax;
(d) Lanolin, its derivatives and components such as acetylated lanolin, lanolin alcohols and lanolin fatty acids.

Lanolin fatty acids are described in U.S. Pat. No. Re. 29,814, Oct. 24, 1978 to W. E. Snyder incorporated herein by reference.
(e) Polyalkylenes such as hydrogenated polyisobutene and polyethylene; and
(f) Sterols such as cholesterol and phytosterol.

These optional oil phase materials may comprise up to about 80% of the oil phase, preferably up to about 35%. When used at these levels, the optional components do not impair the occlusive nature of the compositions and add to the composition's total cosmetic performance.

Water Phase Components

The water phase of the compositions may contain many different materials including:
(a) Humectants, such as sorbitol, glycerine, propylene glycol, alkoxylated glucose and hexanetriol at a level of from about 1% to about 20%.
(b) Thickening agents such as carboxyvinyl polymers, ethyl cellulose, polyvinyl alcohol, carboxymethyl cellulose, vegetable gums and clays such as Veegum.RTM. (magnesium aluminum silicate, R. T. Vanderbilt, Inc.) at a level of from about 0.01% to about 6%;
(c) Proteins and polypeptides at a level of from about 0.1% to about 3%;
(d) Preservatives such as the methyl, ethyl, propyl and butyl esters of hydroxybenzoic acid (Parabens-Mallinckrodt Chemical Corporation) EDTA and imidazolidinyl urea (Germall 115-Sutton Laboratories) at a level of from about 0.2% to about 2.5%; and
(e) An alkaline agent such as sodium hydroxide to neutralize, if desired, part of the fatty acids or thickener which may be present.

All of the percentages of these additional water phase components are of the total composition.

The present compositions may also contain agents suitable for aesthetic purposes such as dyes. The compositions of the present invention are preferably substantially free of materials that adversely affect their performance. Therefore, such things as polyethylene glycols are preferably present only at levels below about 1% of the total composition. The pH of the present compositions is preferably in the range of about 7.5–10.

Method of Manufacture

The compositions which comprise the skin lotion embodiments of the present invention generally have a lotion consistency and may be in the form of oil-in-water or water-in-oil emulsions with the former being preferred because of their more pleasing cosmetic properties. The compositions of the present invention are preferably made by the method comprising the steps of;
a) preparing the oil phase;
b) preparing the water phase; and
c) adding the oil phase to the water phase.

Step (a) is carried out by heating the oil phase materials to a temperature of about 75° C. to about 100° C. Step (b) is carried out by heating the water phase materials to a temperature about the same as that of the oil phase. The emulsion is formed by slowly adding the oil phase prepared in step (a) to the water phase prepared in step (b) with stirring. The pro-accords which comprise the fragrance delivery system or other ingredients may be added to the phase in which they are soluble prior to the mixing of the two phases or added directly to the mixed water and oil phases.

In addition to the fragrance-containing compositions for use on human skin, the pro-accords of the present invention are also suitable for use in any odor controlling or fragrance mediating application. An example of this odor control capacity is animal litter and odor control articles useful in lining the cages, stalls, and other living areas of domesticated animals. For example, U.S. Pat. No. 5,339,769 Toth et al., issued Aug. 23, 1994 describes a process for making an absorbent composition, which can well accommodate the pro-accord materials of the present invention.

An example of a suitable litter material which comprises the pro-accords of the present invention can be formed by the following process.

A Glatt fluid bed granulator is charged with 1,0000 g of bentonite clay (90% of the particles being greater than 420 microns) and 10 g of a cellulose ether (Methocel™ K15M Premium, a cellulose ether having a viscosity of 15,000 centipoise (cps) as a 2% aqueous solution). The granulator is started and the product temperature is brought up to about 40° C. (outlet temperature). When the outlet temperature reaches about 40° C., atomized water is sprayed onto the moving powders within the granulator. During the granulation process, inlet air temperature is maintained at 70° C. to 80° C.; air atomization pressure is 28–35 psi; and the spraying cycle is for 45 seconds with a 15 second shaking time.

The clay/cellulose ether agglomerates swell over time. The water hydrates the cellulose ether polymer, which produces adhesion to form the granule. At this time it is more advantageous to introduce the pro-accord materials and other aesthetic fragrances. The formation of the granule promotes aggregation of the small sized particles of the inert substrate, e.g. clay particles of about 50 to 600 microns. The formation of a granule significantly reduces the quality of dust in the final product while the litter forms an agglomerate when wetted.

In an alternative embodiment of the clay-based litter box articles/pro-accord admixture, once the clay particles have been formed, a concentrated solution, or a carrier alcohol-based admixture of the pro-accords may be delivered to the surface of the granule by a suitable means.

A deodorant gel stick of the present invention having the composition given below, and being essentially free of water, is prepared as follows.

TABLE I

| | Weight % | | |
|---|---|---|---|
| Ingredients | 3 | 4 | 5 |
| Dipropylene glycol | 39.85 | 51.95 | 75.10 |
| Sodium Stearate | 5.50 | 5.50 | 5.50 |
| PPG-3 myristyl ether | 29.40 | 25.33 | 15.00 |
| Cyclomethicone-D5 | 21.00 | 13.33 | — |
| Ethanol (absolute; 200 proof) | 1.80 | 1.44 | 1.95 |
| Zinc pyrithione[1] | 0.05 | 0.05 | 0.05 |
| Pro-fragrance[2] | 2.40 | 2.40 | 2.40 |

[1]Powder form commercially available from Olin.
[2]Pro-accord conjugate according to any of Examples 1–3.

All of the above materials, except the fragrance pro-accord, are vigorously mixed and heated to about 121° C. until the mixture is clear. The mixture is then cooled to about 80° C. and the pro-accord is added with stirring. The mixture is poured into stick molds and cooled to room temperature forming the deodorant gel stick compositions of the present invention.

A personnel cleanser composition is prepared by combining the following ingredients using conventional mixing techniques.

TABLE II

| | Weight % | | | |
|---|---|---|---|---|
| Ingredients | 6 | 7 | 8 | 9 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |
| Methylparaben | 0.200 | 0.200 | 0.200 | 0.200 |
| $C_{10}$–$C_{30}$ alkyl acrylate crosspolymer[1] | 0.150 | 0.150 | 0.150 | 0.150 |
| Carbomer 954[2] | 0.250 | 0.250 | 0.250 | 0.250 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide[3] | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil[4] | — | 5.00 | — | — |
| Phase E | | | | |
| Phenoxyethanol | 0.5 | 0.5 | — | 0.5 |
| Pro-accord[5] | 1.5 | 1.5 | — | — |
| Pro-accord[6] | — | — | 2.20 | 1.5 |
| (if you provide 2 Examples) | | | | |
| Phase F | | | | |
| Glucose amide | 0.96 | 0.96 | 0.96 | 0.96 |

[1]Available as Pemulen ® from B. F. Goodrich Corporation.
[2]Available as Carbomer ® 954 from B. F. Goodrich Corporation.
[3]As a 50% aqueous solution.
[4]Light mineral oil available as Drakeol 5 from Penreco, Dickenson, TX.
[5]Pro-accord conjugate according to any of Examples 1–3.
[6]Pro-accord conjugate according to any of Examples 1–3.

The above examples can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C., and added to the emulsion, which is cooled to room temperature. The resulting cleansing composition is useful for cleansing the skin. The emulsion de-emulsifies upon contact with the skin.

The present invention further relates to the use of photo-labile pro-fragrances in embodiments which do not contact human skin, inter alia, laundry detergent compositions, hard surface cleaning compositions, carpet cleaning compositions, and the like.

Detersive Surfactant

The laundry detergent compositions of the present invention comprise from about 1% by weight, preferably from about 10% to about 80%, preferably to about 60% more preferably to about 30% by weight, of the surfactant system, a surfactant selected from the group consisting of anionic, cationic, nonionic, zwitterionic, ampholytic surfactants, and mixtures thereof. Depending upon the embodiment of the present invention one or more categories of surfactants may be chosen by the formulator. Preferred categories of surfactants are selected from the group consisting of anionic, cationic, nonionic surfactants, and mixtures thereof. Within each category of surfactant, more than one type of surfactant of surfactant can be selected. For example, preferably the solid (i.e. granular) and viscous semi-solid (i.e. gelatinous, pastes, etc.) systems of the present invention, surfactant is preferably present to the extent of from about 1% to 60%, preferably to about 30% by weight of the composition.

Nonlimiting examples of surfactants useful herein include:

a) $C_{11}$–$C_{18}$ alkyl benzene sulfonates (LAS);
b) $C_{10}$–$C_{20}$ primary, branched-chain and random alkyl sulfates (AS);
c) $C_{10}$–$C_{18}$ secondary (2,3) alkyl sulfates having the formula:

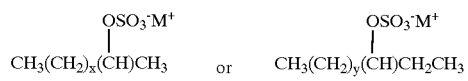

wherein x and (y+1) are integers of at least about 7, preferably at least about 9; said surfactants disclosed in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995 each incorporated herein by reference;

d) $C_{10}$–$C_{18}$ alkyl alkoxy sulfates ($AE_xS$) wherein preferably x is from 1–7;
e) $C_{10}$–$C_{18}$ alkyl alkoxy carboxylates preferably comprising 1–5 ethoxy units;
f) $C_{12}$–$C_{18}$ alkyl ethoxylates, $C_6$–$C_{12}$ alkyl phenol alkoxylates wherein the alkoxylate units are a mixture of ethyleneoxy and propyleneoxy units, $C_{12}$–$C_{18}$ alcohol and $C_6$–$C_{12}$ alkyl phenol condensates with ethylene oxide/propylene oxide block polymers inter alia Pluronic® ex BASF which are disclosed in U.S. Pat. No. 3,929,678 Laughlin et al., issued Dec. 30, 1975, incorporated herein by reference;
g) Alkylpolysaccharides as disclosed in U.S. Pat. No. 4,565,647 Llenado, issued Jan. 26, 1986, incorporated herein by reference;
h) Polyhydroxy fatty acid amides having the formula:

wherein $R^{17}$ is $C_5$–$C_{31}$ alkyl; $R^{18}$ is selected from the group consisting of hydrogen, $C_1$–$C_4$ alkyl, $C_1$–$C_4$ hydroxyalkyl, Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof; preferred Q is derived from a reducing sugar in a reductive amination reaction, more preferably Q is a glycityl moiety; Q is more preferably selected from the group consisting of —$CH_2(CHOH)_n$ $CH_2OH$, —$CH(CH_2OH)(CHOH)_{n-1}CH_2OH$, —$CH_2$ $(CHOH)_2$—$(CHOR')(CHOH)CH_2OH$, and alkoxylated derivatives thereof, wherein n is an integer from 3 to 5, inclusive, and R' is hydrogen or a cyclic or aliphatic monosaccharide, which are described in U.S. Pat. No. 5,489,393 Connor et al., issued Feb. 6, 1996; and U.S. Pat. No. 5,45,982 Murch et al., issued Oct. 3, 1995, both incorporated herein by reference.

Carriers and Adjunct Ingredients

The following are non-limiting examples of adjunct ingredients useful in the laundry compositions of the present invention, said adjunct ingredients include builders, optical brighteners, soil release polymers, dye transfer agents, dispersents, enzymes, suds suppressers, dyes, perfumes, colorants, filler salts, hydrotropes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

The following are non-limiting examples of compositions according to the present invention.

TABLE III

| | weight % | | | |
|---|---|---|---|---|
| Ingredients | 10 | 11 | 12 | 13 |
| Polyhydroxy coco-fatty acid amide | 2.50 | 4.00 | 4.50 | — |
| NEODOL 24-7[1] | — | 4.50 | — | — |
| NEODOL 23-9[2] | 0.63 | — | 4.50 | 2.00 |
| $C_{25}$ Alkyl ethoxylate sulphate | 20.15 | 4.00 | 5.50 | 20.50 |
| $C_{25}$ Alkyl sulfate | — | 14.00 | 15.00 | — |
| C11.8 linear alkylbenzene sulfonate | — | — | — | 6.00 |
| $C_{8-10}$-Amidopropyl Amine | — | 1.30 | — | — |
| $C_{10}$-Amidopropyl Amine | 0.50 | — | — | 1.50 |
| Citric acid | 3.00 | 2.00 | 3.00 | 2.50 |
| C12–18 fatty acid | 2.00 | 6.50 | 5.00 | 5.00 |
| Rapeseed fatty acid | — | 4.10 | — | 6.50 |
| Ethanol | 3.36 | 1.53 | 5.60 | 0.50 |
| Propanediol | 7.40 | 9.20 | 6.22 | 4.00 |
| Monoethanolamine | 1.00 | 7.90 | 8.68 | 0.50 |
| Sodium hydroxide | 2.75 | 1.30 | 0.75 | 4.40 |
| Sodium p-toluene sulfonate | 2.25 | — | 1.90 | — |
| Borax/Boric acid | 2.50 | 2.00 | 3.50 | 2.50 |
| Protease[3] | 0.88 | 0.74 | 1.50 | 0.88 |
| Lipolase[4] | — | 0.12 | 0.18 | — |
| Duramyl[5] | 0.15 | 0.11 | — | 0.15 |
| CAREZYME | 0.053 | 0.028 | 0.080 | 0.053 |
| Dispersant[6] | 0.60 | 0.70 | 1.50 | 0.60 |
| Ethoxylated polyalkyleneimine[7] | 1.20 | 0.70 | 1.50 | 1.20 |
| Optical Brightener | 0.13 | 0.15 | 0.30 | 0.15 |
| Pro-fragrance[8] | 1.0 | 1.5 | — | — |
| Pro-fragrance[9] | — | — | 0.5 | 0.7 |
| Suds suppresser | 0.12 | 0.28 | 0.12 | 0.12 |
| Minors, aesthetics, stabilizers, water | balance | balance | balance | balance |

[1]$C_{12}$–$C_{14}$ alkyl ethoxylate as sold by Shell Oil Co.
[2]$C_{12}$–$C_{13}$ alkyl ethoxylate as sold by Shell Oil Co.
[3]Protease B variant of BPN' wherein Tyr 17 is replaced with Leu.
[4]Derived from Humicola lanuginosa and commercially available from Novo.
[5]Disclosed in WO 9510603 A and available from Novo.
[6]Hydrophilic dispersant PEI 189 $E_{15}$–$E_{18}$ according to U.S. Pat. No. 4,597,898, Vander Meer, issued Jul. 1, 1986.
[7]Polyalkyleneimine dispersant PEI 600 $E_{20}$.
[8]According to Example 1.
[9]According to Example 2.

As a non-limiting example, granular compositions are generally made by combining base granule ingredients, e.g., surfactants, builders, water, etc., as a slurry, and spray drying the resulting slurry to a low level of residual moisture (5–12%). The remaining dry ingredients, e.g., granules of the polyalkyleneimine dispersant, can be admixed in granular powder form with the spray-dried granules in a rotary mixing drum. The liquid ingredients, e.g., solutions of the polyalkyleneimine dispersant, enzymes, binders and perfumes, can be sprayed onto the resulting granules to form the finished detergent composition. Granular compositions according to the present invention can also be in "compact form", i.e. they may have a relatively higher density than conventional granular detergents, i.e. from 550 to 950 g/l. In such case, the granular detergent compositions according to the present invention will contain a lower amount of "inorganic filler salt", compared to conventional granular detergents; typical filler salts are alkaline earth metal salts of sulphates and chlorides, typically sodium sulphate; "compact" detergents typically comprise not more than 10% filler salt.

Liquid detergent compositions can be prepared by admixing the essential and optional ingredients thereof in any desired order to provide compositions containing components in the requisite concentrations. Liquid compositions according to the present invention can also be in "compact form", in such case, the liquid detergent compositions according to the present invention will contain a lower amount of water, compared to conventional liquid detergents. Addition of the polyalkyleneimine dispersant to liquid detergent or other aqueous compositions of this invention may be accomplished by simply mixing into the liquid solutions the polyalkyleneimine dispersant.

The compositions of the present invention can be suitably prepared by any process chosen by the formulator, non-limiting examples of which are described in U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

What is claimed is:

1. A photo-activated pro-accord conjugate having the formula:

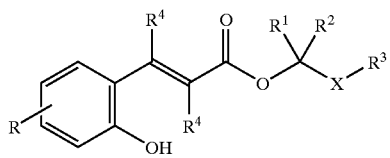

wherein:
a.) X is:
   i) —$NR^7$—;
   ii) —NH—;
   iii) —S—;
   iv) —$N(R^8)_2$—
   v) or mixtures thereof;
   wherein $R^7$, and each $R^8$ is independently selected from $C_1$–$C_{20}$ substituted or unsubstituted, linear or branched, cyclic or acyclic hydrocarbyl; $C_3$–$C_{20}$ substituted or unsubstituted, cyclic or acyclic heterocarbyl; $C_6$–$C_{20}$ substituted or unsubstituted alkaryl, aryl or aralkyl;
   or mixtures thereof;
b.) R is a photo-labile unit modulating group;
c.) $R^1$ is selected from:
   i) $C_1$–$C_{20}$ substituted or unsubstituted, linear or branched, cyclic or acyclic hydrocarbyl;
   ii) $C_3$–$C_{20}$ substituted or unsubstituted, cyclic or acyclic heterocarbyl;
   iii) or mixtures thereof;
d.) $R^2$ is selected from:
   i) hydrogen;
   ii) $R^1$;

wherein $R^1$ and $R^2$ are moieties when taken together with a carbonyl moiety comprise an aldehyde or a ketone having the formula:

$$R^1R^2C=O$$

which is capable of being released by said photo labile compound; and
e.) $R^3$ is selected from:
   i) $C_1$–$C_{20}$ substituted or unsubstituted, linear or branched, cyclic or acyclic hydrocarbyl;
   ii) $C_3$–$C_{20}$ substituted or unsubstituted, cyclic or acyclic heterocarbyl;
   iii) hydrogen;
   iv.) or mixtures thereof;
   wherein when any 2 or more moieties selected from any non-hydrogen $R^3$, $R^7$ or $R^8$, combine, said moieties form a common ring;
f.) $R^4$ is selected from:
   i) hydrogen;
   ii) halogen;
   iii) —OR';
   iv) —$N(R')_2$;
   v) —SR';
   vi) nitrilo;
   vii) a carbonyl comprising unit having the formula:

$$-(CH_2)_xCOR^6$$

wherein $R^6$ is hydrogen, —OR', —$N(R')_2$, $C_1$–$C_{20}$ substituted or unsubstituted, linear or branched, cyclic or acyclic hydrocarbyl, $C_3$–$C_{20}$ substituted or unsubstituted, cyclic or acyclic heterocarbyl, or mixtures thereof;
   viii) $C_1$–$C_{20}$ substituted or unsubstituted, linear or branched, cyclic or acyclic hydrocarbyl;
   ix) or mixtures thereof.

2. A conjugate according to claim 1 wherein X is —NH— or —$NR^7$—.

3. A conjugate according to claim 1 wherein R is selected from:
   a.) hydrogen;
   b.) halogen;
   c.) —OR';
   d.) —$N(R')_2$;
   e.) —SR';
   f.) —CN;
   g.) —$NO_2$;
   h.) —C(O)R';
   i.) —C(O)OR';
   j.) —OC(O)R';
   k.) —$SO_2$R';
   l.) —$SO_3$R';
   m.) —$OSO_2$R';
   n.) $C_1$–$C_{20}$ substituted or unsubstituted, linear or branched, cyclic or acyclic hydrocarbyl;
   o.) $C_1$–$C_{20}$ substituted or unsubstituted, linear or branched, cyclic or acyclic heterocarbyl;
   p.) or mixtures thereof;
   wherein R' is hydrogen, $C_1$–$C_{20}$ hydrocarbyl, —OH, and mixtures thereof.

4. A conjugate according to claim 3 wherein R is —OH, $C_1$–$C_{20}$ substituted or unsubstituted, linear or branched, cyclic or acyclic hydrocarbyl; or mixtures thereof.

5. A conjugate according to claim 4 wherein R is —OH.

6. A conjugate according to claim 2 wherein $R^1$ and $R^2$ are moieties when taken together with a carbonyl moiety comprise a ketone.

7. A conjugate according to claim 2 wherein $R^1$ and $R^2$ are moieties when taken together with a carbonyl moiety comprise an aldehyde.

8. A conjugate according to claim 2 wherein $R^3$ is a unit derived from a fragrance raw material alcohol.

9. A conjugate according to claim 2 wherein X is —NH—.

10. A conjugate according to claim 9 wherein $R^1$ and $R^2$ are moieties when taken together with a carbonyl moiety comprise a ketone.

11. A conjugate according to claim 9 wherein $R^1$ and $R^2$ are moieties when taken together with a carbonyl moiety comprise an aldehyde.

12. A system comprising a photo-activated pro-accord conjugate according to claim 1.

13. The system of claim 12, wherein said system comprises a product selected from the group consisting of a hair care product, beauty care product, a laundry or cleaning product, a food or beverage product, a paper product, or a pet care product.

14. The system of claim 13, wherein said system comprises a product selected from the group consisting of a cream, a lotion, a deodorant, an antiperspirant, a nail polish, a hair spray, a hair gel, a leave-in conditioner, a fabric static control sheet, a fabric refresher spray, a carpet refresher spray, an air freshener, a diaper, a toilet paper, a cleaning wipe; a food, a coffee, a pet food, a body wash, a bar soap, a hair shampoo, a body shampoo, a hair conditioner, a body conditioner, a pet shampoo, a pet conditioner, a hair colorant, a laundry detergent, a fabric softener, a hard surface cleaner, or a carpet cleaner.

15. A method of delivering a photo-activated pro-accord conjugate to a situs, said method comprising the step of contacting a situs with the photo-activated pro-accord conjugate of claim 1.

16. A method for delivering an accord to a situs, said method comprising the steps of:

a.) delivering to a situs a photo-activated pro-accord conjugate according to claim 1; and b.) exposing said photo-activated pro-accord conjugate to electromagnetic radiation capable of initiating release of said fragrance raw materials.

* * * * *